(12) United States Patent
Skiera

(10) Patent No.: US 6,827,343 B2
(45) Date of Patent: Dec. 7, 2004

(54) TORSION DEVICE OF AN EXOPROSTHESIS

(75) Inventor: Richard Skiera, Vienna (AT)

(73) Assignee: Otto Bock HealthCare GmbH, Duderstadt (DE)

( * ) Notice: Subject to any disclaimer, the term of this patent is extended or adjusted under 35 U.S.C. 154(b) by 372 days.

(21) Appl. No.: 10/184,074

(22) Filed: Jun. 28, 2002

(65) Prior Publication Data

US 2003/0018393 A1 Jan. 23, 2003

(30) Foreign Application Priority Data

Jun. 29, 2001 (DE) .......................................... 101 31 159

(51) Int. Cl.[7] .............................. F16F 1/14; A61F 2/60; A61F 2/66
(52) U.S. Cl. ........................... 267/154; 623/35; 623/52; 248/608
(58) Field of Search ................................ 267/154, 284; 248/608, 609; 623/35, 52, 27

(56) References Cited

U.S. PATENT DOCUMENTS

| 3,956,775 A | 5/1976 | Moore |
| 4,038,705 A | 8/1977 | Owens et al. |
| 4,134,159 A | 1/1979 | Wilson |
| 5,800,563 A | 9/1998 | Arbogast et al. |

FOREIGN PATENT DOCUMENTS

| EP | 196 37 173 A1 | 9/1996 |
| EP | 2 305 363 A | 4/1997 |
| GB | 1386333 | 9/1972 |
| WO | WO 98/29059 | 7/1998 |
| WO | WO 98/56320 | 12/1998 |

OTHER PUBLICATIONS

European Search Report dated Oct. 23, 2002.

*Primary Examiner*—David H. Willse
(74) *Attorney, Agent, or Firm*—Whitham, Curtis & Christofferson, PC

(57) ABSTRACT

The invention relates to a torsion device of an exoprosthesis system, with a proximal part (1) which, counter to the action of a resilient torsion element, can be turned in positive and negative directions of rotation (5, 6) in relation to a distal part (2). To increase the functional range, it is proposed that the torsion element (4), in the positive direction of rotation (5), has a torsion characteristic different than that in the negative direction of rotation (6).

23 Claims, 1 Drawing Sheet

SECTION A-A

SECTION B-B

TORSION DEVICE OF AN EXOPROSTHESIS

The invention relates to a torsion device of an exoprosthesis, with a proximal part which, counter to the action of a resilient torsion element, can be turned in positive and negative directions of rotation in relation to a distal part, the torsion element having, in the positive direction of rotation, a torsion characteristic different than that in the negative direction of rotation.

Shock absorbers are used in exoprostheses for cushioning and absorbing the ground reaction forces. During walking, running or jumping, ground reaction forces caused by ground contact act via the prosthesis and the shaft on the stump and on the rest of the body. Cushioning and absorption of this loading of the sensitive stump and body can help to reduce stump problems, to avoid overloading of the muscles and skeletal apparatus and to improve patient comfort. In the case of above-knee amputees, the rotation capacity of the device compensates for the lack of rotation capacity of the hip joint as a result of the rigid stump-shaft connection at the pelvis. Here, the internal rotation of the foot relative to the pelvis during the stance phase of a walking cycle is of particular importance. In field studies, an increased rotational rigidity (locking moment or initial moment) for small excursions of the shock absorber is considered by patients as very pleasant and stabilizing.

The torsion device described at the outset can be gathered from DE 196 37 173 A1. The latter discloses a prosthesis pylon with a compressible fluid volume contained therein for supporting the weight of a patient. This pylon includes a first end portion which can be secured to the leg stump of the patient, and a second end portion which lies opposite the first end portion and can be connected to a prosthetic foot and can turn relative to the first end portion about a longitudinal axis of the pylon. The first end portion and second end portion are coupled via a torsion spring which with a first spring rate resists a rotation in the clockwise direction and with a second spring rate resists a rotation in the counterclockwise direction, which second spring rate is chosen such that it is chosen differently from the first spring rate depending on whether the leg stump of the patient is a right or left leg stump.

The object of the invention is to improve the functionality of the torsion device described at the outset.

Starting from the torsion device described at the outset, this object is achieved, according to the invention, by the fact that the torsion element comprises two separate torsion spring elements which have different spring characteristics and are each fitted, with prestressing, between their associated abutments in such a way that in each case only one of the two torsion spring elements is active in one of the two directions of rotation, namely only in the positive direction of rotation or only in the negative direction of rotation.

In this definition of the invention, and also in the description which follows, the proximal part could also represent a distal part and the distal part could represent a proximal part; and a torsion spring element could also include a group of torsion spring elements.

The term "resilient" is intended to cover elastic and/or viscoelastic and/or friction-adhering spring elements and a viscoplasticity.

In a special embodiment, the two torsion spring elements can be formed by two ring segments which are made of an elastomer and which, viewed in the direction of rotation, bear directly or indirectly on a carrier of the proximal part and on an abutment fixed in a stationary position on the distal part.

To achieve a compact embodiment and a reliable function, it is advantageous if the two torsion spring elements bear with their respective first end on circumferentially opposite sides of the abutment and bear with their respective second end on a respective second abutment, these second abutments being mounted on the distal part in such a way that they can each be displaced in the circumferential direction by at least several circumferential degrees relative to the torsion spring element bearing on them.

To adapt the characteristics to the requirements of the patient, it is expedient for the torsion spring elements to be exchangeable.

In a further embodiment, it is expedient if the second abutments are mounted so as to be displaceable in the circumferential direction in such a way that in each case only one of these abutments can be displaced relative to the torsion spring element bearing on it, while the other second abutment remains held, with prestressing, by a further abutment. This solution results in a markedly high initial rigidity.

According to the invention, the rotation properties of the torsion device can thus be adapted individually, e.g. in terms of internal and external rotation. The different torsional rigidities that can be set thus afford the possibility of permitting a "soft" internal rotation and of obtaining more stability by means of a "hard" external rotation during heel contact and toe take-off. An important factor in terms of the stability felt by the patient is that there is no appreciable rotation under slight torsional moments. The action of the torsion spring elements, dependent on the direction of rotation, which can be achieved according to the invention permits, in conjunction with their prestressing, the creation of a locking moment which is likewise dependent on the direction of rotation.

Since, in addition to the loading caused by torsional moments, axial forces also act in a shocklike manner on the exoprosthesis and the human apparatus of locomotion, it is advantageous if the torsion device is combined with a shock absorber system which has an axial spring element which bears with its distal end on the distal part and bears with its proximal end on the proximal part guided telescopically in the distal part.

Further features of the invention are the subject of the dependent claims and are explained in greater detail, together with further advantages of the invention, with reference to an illustrative embodiment.

An embodiment of the invention which will serve as an example is shown in the drawing, in which.

Figure 1:
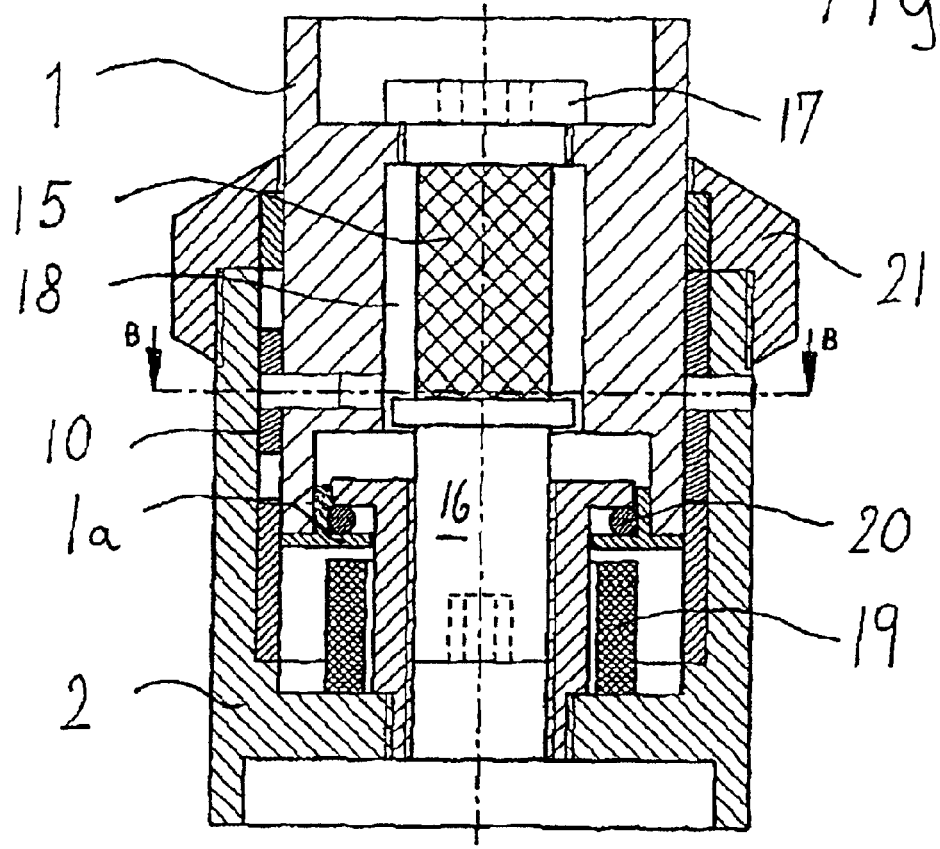
FIG. 1 shows a torsion device in longitudinal section.

The torsion device shown comprises a proximal part 1 which is guided axially in a telescopic manner in a distal part 2. The two parts 1, 2 can turn in positive and negative directions of rotation relative to one another counter to the action of a resilient torsion element. When this torsion device is used, for example in a below-knee prosthesis, the proximal part 1 can be connected to the stump of a prosthesis wearer, while the distal part 2 is connected to a prosthetic foot.

In the illustrative embodiment shown, the torsion element comprises two separate torsion spring elements 3, 4 which have different spring characteristics and of which in each case only one torsion spring element is active in one of the two directions of rotation, namely only in the positive direction of rotation 5 or only in the negative direction of rotation 6. The two torsion spring elements 3, 4 are formed by two ring segments which are made of an elastomer and which bear with their respective first end on circumferentially opposite sides 7a, 7b of an abutment 7 fixed in a stationary position on the distal part 2, while they bear with their respective second end on a respective second abutment 8, 9. These second abutments 8, 9 are mounted on the distal part 2 in such a way that they can each be displaced in the circumferential direction by at least several degrees relative to the torsion spring element 3 or 4 bearing on them. The two displaceable second abutments 8, 9 bear on a carrier 10 which acts upon them in a relative rotational movement and is secured on the proximal part 1.

Figure 2:
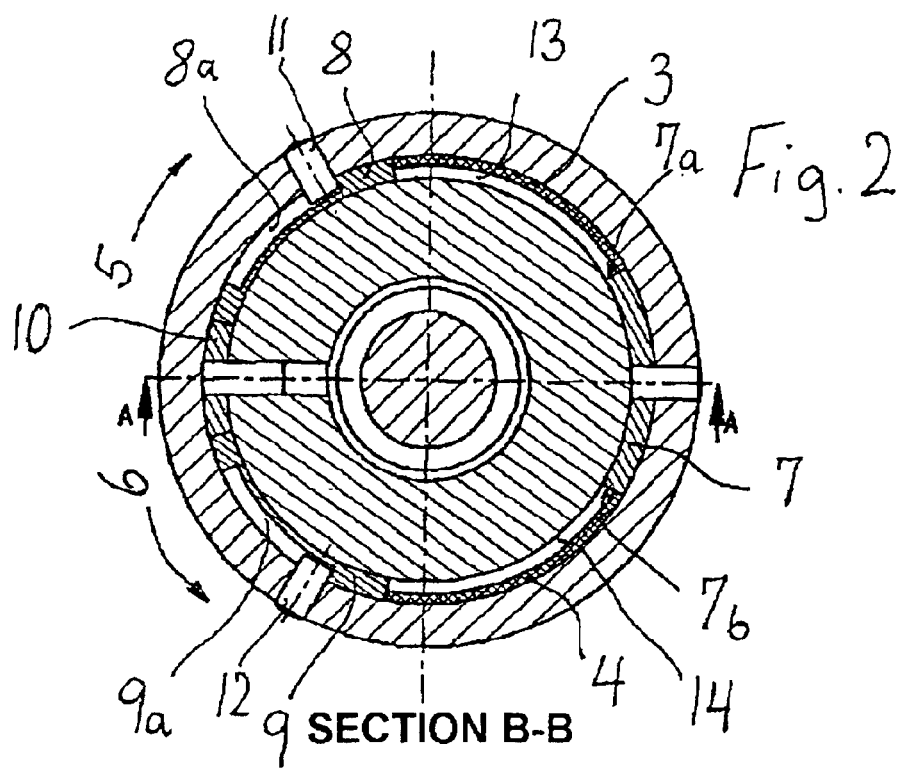
FIG. 2 shows the torsion device according to FIG. 1 in cross section along the line B—B in FIG. 1.

The torsion spring elements 3, 4 are fitted with prestressing between their assigned abutments 7, 8 and 7, 9, respectively on circumferentially opposite sides. In a particular embodiment, the second abutments 8, 9 can be mounted so as to be displaceable in the circumferential direction such that in each case only one of these abutments is displaceable relative to the torsion spring element 3 or 4 bearing on it, while the other second abutment remains held, with prestressing, by a further abutment 11 or 12. According to FIG. 2, these two further abutments 11, 12 are each designed as a pin which is arranged fixedly in the distal part 2 and with its free end protrudes inward into a displacement groove 8a, 9a of the second abutment 8 or 9, respectively.

The torsion spring elements 3, 4 are exchangeable, so that in principle it is also possible to replace one of these torsion spring elements with a substantially rigid element which then as it were blocks the rotation of the two parts 1, 2 in one of the two directions of rotation 5, 6.

In the illustrative embodiment shown, the torsion spring elements 3, 4 are made of a substantially incompressible elastomer and, when subjected to torsion by the carrier 10, buckle into a free space 13, 14, respectively, which is provided for this purpose in the construction and can be dimensioned such that the shallow rise of the spring characteristic curve of the torsion spring elements 3, 4 at the end of the torsion merges into a strongly progressive rise.

In principle it is possible that the two displaceable abutments 8, 9 at the same time form bearing shells for the proximal part 1, which is pushed with a tubular attachment piece into the distal part 2.

The carrier 10 is inserted exactly, or with overdimensioning, between the two displaceable abutments 8, 9.

The torsion device shown is also equipped with a shock-absorber system which has an axial spring element 15 which bears with its distal end on the head of a prestressing screw 16 screwed into the proximal part 1 and bears with its proximal end on a closure screw 17 screwed into the proximal part 1. By means of the prestressing screw 16, a prestressing can be applied steplessly to the axial spring element 15. The closure screw 17 is used to close off an opening through which the axial spring element 15 can be exchanged.

The axial spring element 15 is formed by an elastomeric rod which is made of a substantially incompressible elastomer and, when acted upon axially, buckles into a free space which is provided for this purpose in the construction and which can be dimensioned such that the shallow rise of the spring characteristic curve of the elastomeric rod at the end of the axial spring compression merges into a strongly progressive rise.

The maximum axial spring compression is limited by a nonlinear end contact spring element 19 which is formed by an elastomeric ring fixed in the distal part 2. When the torsion device is free from axial force, the proximal part 1 rests with an annular shoulder 1a on an upper contact element 20 which limits the travel. A screw cap 21 is also provided which is screwed onto the proximal end of the distal part 2 and forms part of the telescopic guide for the proximal part 1.

What is claimed is:

1. Torsion device of an exoprosthesis, with a proximal part (1) which, counter to the action of a resilient torsion element, can be turned in positive and negative directions of rotation (5, 6) in relation to a distal part (2), the torsion element having, in the positive direction of rotation (5), a torsion characteristic different than that in the negative direction of rotation (6), characterized in that the torsion element comprises two separate torsion spring elements (3, 4) which have different spring characteristics and are each fitted, with prestressing, between associated abutments (7, 8 and 7, 9, respectively) in such a way that in each case only one of the two torsion spring elements (3 or 4) is active in one of the two directions of rotation (5 or 6), namely only in the positive direction of rotation or only in the negative direction of rotation.

2. Torsion device according to claim 1, characterized in that the two torsion spring elements (3, 4) are formed by two ring segments which are made of an elastomer and which, viewed in the direction of rotation, bear directly or indirectly on a carrier (10) of the proximal part (1) and on an abutment (7) fixed in a stationary position on the distal part (2).

3. Torsion device according to claim 2, characterized in that the two torsion spring elements (3, 4) bear with respective first ends thereof on circumferentially opposite sides (7a, 7b) of the abutment (7) and with respective second ends thereof on respective second abutments (8, 9), these second abutments (8, 9) being mounted on the distal part (2) in such a way that they can each be displaced in the circumferential direction by at least several circumferential degrees relative to the torsion spring element (3, 4) bearing on them.

4. Torsion device according to claim 3, characterized in that the second abutments (8, 9) are mounted so as to be displaceable in the circumferential direction in such a way that in each case only one of these abutments can be displaced relative to the torsion spring element (3, 4) bearing on it, while the other second abutment remains held, with prestressing, by a further abutment (11, 12).

5. A torsion device according to claim 4, characterized in that said carrier is inserted exactly, or with overdimensioning, between the two displaceable abutments.

6. A torsion device according to claim 3, characterized in that, in order to act upon the two displaceable second abutments, a carrier is provided which is fixed on the proximal part.

7. A torsion device according to claim 2, characterized in that the torsion spring elements are made of a substantially incompressible elastomer and, when subjected to torsion by the carrier, buckle into a free space provided for this purpose in the construction.

8. Torsion device according to claim 7, characterized in that said free space (13, 14) is dimensioned such that a shallow rise of the spring characteristic curve merges into a strongly progressive rise at the end of the torsion.

9. A torsion device according to claim 3, characterized in that the two displaceable abutments at the same time form bearing shells for the proximal part inserted with a tubular attachment piece into the distal part.

10. A torsion device according to claim 1, characterized in that only one common first abutment is provided for the two torsion spring elements.

11. A torsion device according to claim 1, characterized in that the torsion spring elements are exchangeable.

12. A torsion device according to claim 1, characterized by a shock-absorber system which has an axial spring element which bears with a distal end on the distal part and bears with a proximal end on the proximal part guided telescopically in the distal part.

13. Torsion device according to claim 12, characterized in that the axial spring element (15) is exchangeable.

14. A torsion device according to claim 12, characterized by a prestressing screw by means of which a prestressing can be applied steplessly to the axial spring element.

15. A torsion device according to claim 12, characterized in that the proximal part has an opening which is used for exchanging the axial spring element and which can be closed off by a closure screw.

16. Torsion device according to claim 15, characterized in that the closure screw (17) at the same time forms a prestressing screw.

17. A torsion device according to claim 12, characterized in that the maximum axial spring compression i8s limited by an end-stop spring element.

18. Torsion device according to claim 17, characterized by a nonlinear end-stop spring element (19).

19. A torsion device according to claim 17, characterized in that the end-stop spring element is formed by an elastomeric ring fixed in the distal part.

20. A torsion device according to claim 12, characterized in that, with the torsion device free from axial force, the proximal part bears with an annular shoulder on an upper contact spring element which limits the travel.

21. A torsion device according to claim 12, characterized by a screw cap which forms a telescopic guide for a proximal part and which is screwed onto the proximal end of the distal part.

22. A torsion device according to claim 12, characterized in that the axial spring element is formed by an elastomeric rod.

23. Torsion device according to claim 22, characterized in that the elastomeric rod (15) is made of a substantially incompressible elastomer and, when acted upon axially, buckles into a free space (18) which is provided for this purpose in the construction and which is dimensioned such that a shallow rise of the spring characteristic curve at the end of the axial compression merges into a strongly progressive rise.

* * * * *